United States Patent [19]

Leonard

[11] Patent Number: 4,515,154

[45] Date of Patent: May 7, 1985

[54] METHOD AND APPARATUS FOR INDEXING THE CONDYLE POSITION DURING SAGITTAL RAMUS SPLIT SURGERY

[76] Inventor: Myer S. Leonard, 1340 Fairlawn Way, Golden Valley, Minn. 55416

[21] Appl. No.: 501,655

[22] Filed: Jun. 6, 1983

[51] Int. Cl.³ .............................................. A61F 5/04
[52] U.S. Cl. ................................ 128/92 EB; 433/73; 128/92 R
[58] Field of Search .............. 128/92 EB, 92 R, 92 B, 128/92 C, 92 EA; 433/72, 73

[56] References Cited

U.S. PATENT DOCUMENTS

| | | | |
|---|---|---|---|
| 2,362,741 | 11/1944 | Berke | 128/92 R |
| 2,502,902 | 4/1950 | Tofflemire | 128/92 R |
| 4,335,715 | 6/1982 | Kirkley | 128/92 EB |
| 4,368,041 | 1/1983 | Roup | 433/73 X |
| 4,411,622 | 10/1983 | Hansen | 433/73 |

OTHER PUBLICATIONS

Leonard, Oral Surgery, vol. 34, p. 942, "Preventing Rotation of the Proximal . . . ", Oct., 1976.

*Primary Examiner*—Edward M. Coven

[57] ABSTRACT

The method and apparatus for positionally indexing the upper segment of the split ramus with respect to the maxilla, during a sagittal split ostotomy, to insure proper occlusal position of the condyle which includes positively anchoring a template to a substantial portion of the maxillary arch and providing a rearwardly-extending indexing paddle fixed to the template to overlie the ramus to permit positive indexing reference of the occlusal position of the condyle required for successful completion of the operation.

4 Claims, 6 Drawing Figures

METHOD AND APPARATUS FOR INDEXING THE CONDYLE POSITION DURING SAGITTAL RAMUS SPLIT SURGERY

BACKGROUND OF THE INVENTION

For a number of years, oral surgeons have been correcting retrognathic and prognathic mandible conditions by performing a sagittal split ostotomy during which the ramus bone is split and either lengthened or shortened to correct the abnormal condition by shifting the mandible forwardly or rearwardly as may be required. When the masseter is stripped away from the ramus and the ramus is split, the condyle will move out of its seated relationship in the temporal fossa and it is extremely difficult to be sure that the condyle is returned to its proper reseated position and orientation after the split-apart ramus bone segments are realigned and connected after making the desired length correction.

This invention has been developed to provide a positive indexing reference with respect to the maxilla to permit the accurate repositioning of the condyle in the temporal fossa.

SUMMARY OF THE INVENTION

The apparatus embodying this invention is designed to provide a positive indexing reference for the upper segment of the ramus during a sagittal split ostotomy of the ramus. The apparatus includes an anchoring template which is adjustable to different sized jaws and which is particularly designed for positive attachment to a substantial portion of the maxillary arch of the patient to provide a positive positioning anchor for the template. An indexing paddle is positively fixed to the rear segment of the anchoring template and extends rearwardly therefrom to overlie the exposed ramus bone surface. The upper edge of the indexing paddle is approximately aligned with the gum line of the maxillary teeth and in the form shown, the paddle is approximately 5 mm wide, which has been found to be a convenient width. The ramus bone segment is then marked along both the top and bottom edges of the paddle to provide positive indexing lines to insure precise repositioning of the ramus after completion of the corrective splicing operation and insure replacement of the condyle back into its temporal fossa socket.

The method for performing a sagittal ramus split operation embodying this invention includes stripping away the masseter tissue from the ramus bone, positively anchoring an indexing paddle element to a major portion of the maxillary teeth, marking the exterior surface of the exposed portion of the ramus bone along the edges of the indexing paddle to provide a precisely accurate repositioning reference, splitting the ramus into two segments, adjusting the relative position of the two ramus segments to correct the irregular formation of the mandible and shift the mandible into its desired corrected position, re-registering the indexing lines on the ramus surface with the edges of the indexing paddle, positively connecting the two ramus segments for ultimate healing in its correct occlusal position with the reference lines in registration with the paddle to insure proper seating of the condyle in the temporal fossa after completion of the operation.

DETAILED DESCRIPTION OF THE PREFERRED EMBODIMENT

Figure 1:
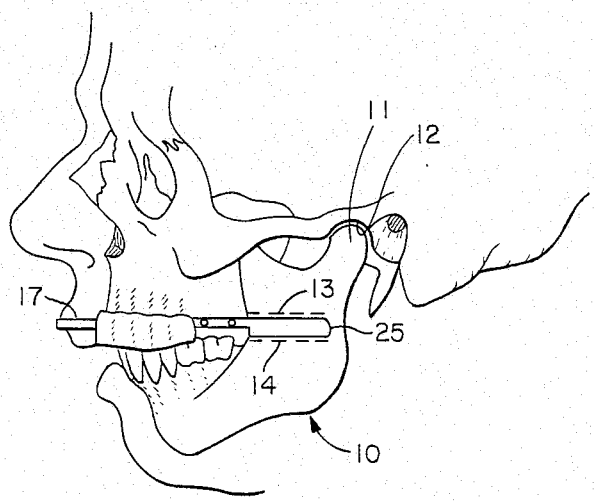
FIG. 1 is a side elevational view of a preoperative retrognathic mandible condition.

A typical retrognathic condition is illustrated in FIG. 1 showing the retracted lower jaw structure with the left ramus 10 having its condyle ball segment 11 received in its normal position in the temporal fossa socket 12.

Figure 4:
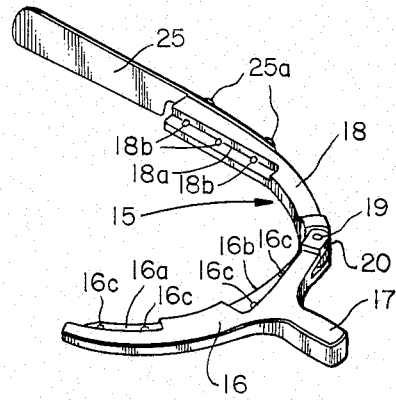
FIG. 4 is a perspective view of the left side indexing template and paddle assembly.

The maxillary teeth are designated by the reference numeral 9. A left side indexing template 15 is illustrated in perspective in FIG. 4 and includes an anchoring segment 16 contoured to fit against the right side of the maxillary teeth 9 with its upper edge slightly downwardly from the upper gum line to permit positive attachment to the right maxillary teeth by suitable means such as an acrylic resin cement, for example, the cement known as Orthodontic Resin manufactured by L. D. Caulk Company, of Milford, Del. Suitable cement-receiving pockets or recesses 16a and 16b are provided which have anchoring holes 16c provided therein for positively receiving the cement materials. A gripping handle 17 is provided to assist in the initial positioning until the cement has hardened. The template 15 has a second section 18 pivotally connected to the left end of the segment 16 as by a pivot pin 19 which extends through a suitable tongue and clevice joint assembly designated by the numeral 20. The left side segment 18 overlies the left maxillary teeth with the upper edge portion spaced downwardly from the maxillary gum line as illustrated and is provided with a recess 18a and anchoring holes 18b as best shown in FIG. 4. The hinge pin 19 permits the segment 18 to conform to jaws of different sizes in order to provide a relatively close-fitting relationship between the inner edge of the segment 18 and the left maxillary teeth. The segments 16 and 18 are sufficiently thin to permit the same to be mounted in operative position above orthodontia braces which may be in place in the patient's mouth, thus avoiding the necessity for removal of the braces prior to the operation.

The masseter tissue is stripped away from the surface of the ramus so that the surface is exposed. After the segments 16 and 18 have been positively anchored to the maxillary teeth as by the appropriate cement material, the paddle element 25 fixed in rearwardly-extending relation to the rear end portion of the segment 18 as by attachment screws 25a, will be positioned in overlying relation to the ramus bone 10 as best shown in FIG. 1.

Figure 2:
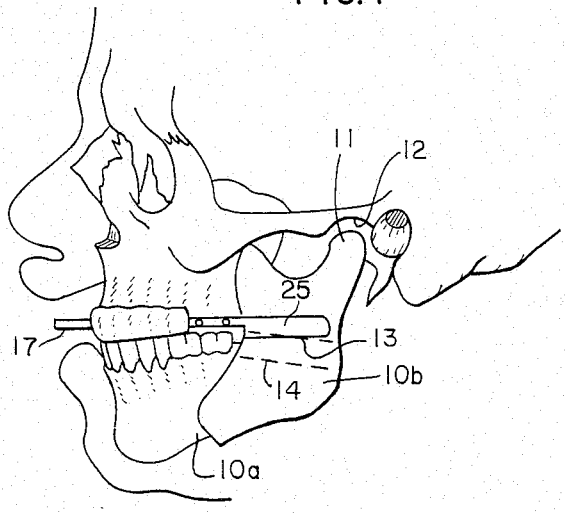
FIG. 2 is a similar view of the jaw shown in FIG. 1 with the condyle displaced after splitting the ramus during the operative procedure.
Figure 3:
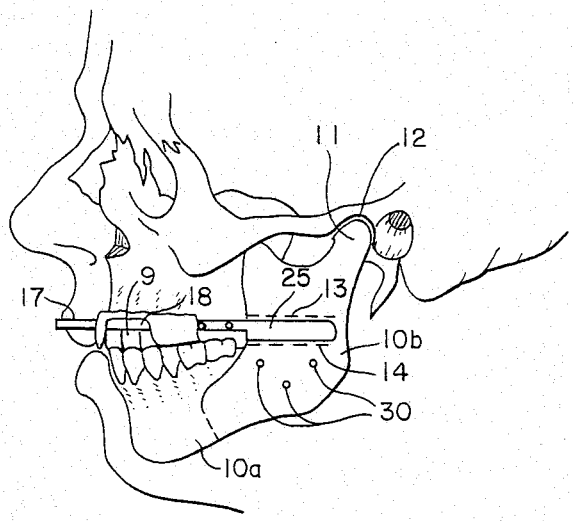
FIG. 3 is a similar view with the condyle repositioned in its proper position in its temporal fossa socket.
Figure 6:
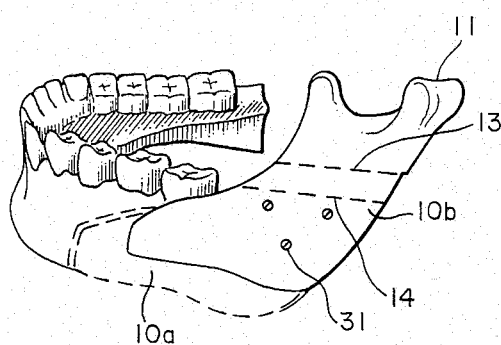
FIG. 6 is a perspective view of a lower jaw structure after completion of the operation.

With the paddle element in place, indexing marks are applied to the exposed surface of the ramus 10 along the top and bottom edges of the paddle 25. The dotted lines 13 and 14 represent these indexing marks. A reciprocating saw such as a Stryker saw, or a bur such as a Toller bur, may be used to produce the marks on the ramus surface. The surgeon then completes the sagittal ramus split operative procedure in the normal way and moves the lower jaw portion 10a forwardly or rearwardly as the condition requires. The retrognathic condition illustrated in the drawings requires that the lower jaw segment be moved forwardly into proper alignment with the maxillary teeth as shown in FIGS. 3 and 6. FIG. 2 illustrates the shifting movement of the condyle 11 into its temporal fossa socket 12 which is a condition that occurs at the time the ramus is split into two sections 10a and 10b.

The position of the indexing paddle 25 provides the positive fixed reference necessary to insure proper replacing of the condyle in its temporal fossa. This is accomplished by aligning the two indexing lines 13 and 14 with the edges of the paddle 25 as shown in FIG. 3 and holding the two sections 10a and 10b in fixed relationship as by conventional bone-holding clamping forceps while anchoring holes 30 are drilled therein. The holes through the upper ramus section 10b, which is positioned in overlapping, outside relationship to the lower section 10a as illustrated, are slightly larger than the holes drilled in the inner section to provide clearance for anchoring screws 31 to pass therethrough. The holes in the inner bone section have screw matching threads tapped therein to facilitate insertion of the anchoring screws 31 without danger of splitting the bone structure of either of the ramus sections 10a and 10b. The use of three anchoring screws 31 has worked satisfactorily to provide positive positioning of the bone sections 10a and 10b during the reuniting healing process of the ramus sections in their corrected occlusal position.

Figure 5:
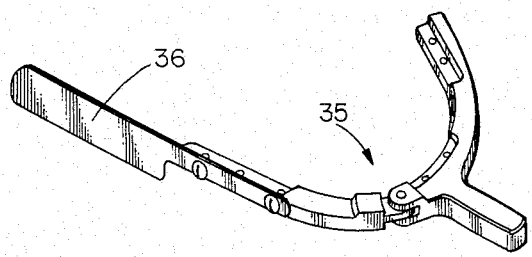
FIG. 5 is a perspective view of the right side indexing template and paddle assembly.

After the surgery has been completed on one side, the template is removed and the operation may be repeated on the opposite side of the patient's jaw structure. A right side indexing template 35 is illustrated in FIG. 5 and has a right side indexing paddle 36 similar to the indexing paddle for the left side template 15. All of the other template elements described in connection with template 15 are provided in the construction of the template 35 and, therefore, the description thereof will not be repeated.

It will be seen that I have provided an effective method and apparatus for insuring proper repositioning of the condyle 11 in its temporal fossa socket 12 during the final reconnection of the two ramus bone segments during sagittal ramus split surgery.

It is to be understood that while there has been illustrated and described certain forms of the present invention, the invention is not to be limited to the specific form or arrangement of parts herein described and shown except to the extent that such limitations are found in the claims.

What is claimed is:

1. The method for providing a positive position indexing reference for sagittal ramus split surgery comprising,
    providing an indexing template which includes means for adjusting the size thereof to fit different size maxillary arch structures,
    placing the template in contact with the front surfaces of the maxillary arch teeth,
    conforming the template to the shape and size of the arch,
    positively anchoring the template to the teeth of the maxillary arch to provide a fixed reference anchor,
    attaching a rearwardly extending indexing paddle to the template in overlapping relation to the ramus,
    marking the outer surface of the ramus along the edges of the indexing paddle with a pair of indexing lines to positively indicate the occlusal position and angular relationship of the condyle in the temporal fossa socket,
    splitting the ramus into two sections having an overlapping adjustment portion,
    adjusting the two sections to correct the abnormal mandible condition,
    repositioning the two split-apart ramus sections with the two reference indexing lines realigned with the indexing paddle,
    reconnecting the split-apart ramus sections in their corrected occlusal position,
    the two split-apart ramus sections being reconnected by a plurality of screws after drilling holes through the overlapping portion of the upper ramus section slightly larger than the diameter of the anchoring screws,
    drilling and tapping holes in the overlying lower ramus section aligned with the larger outer holes to threadably receive the screws therein, and
    positively attaching the two overlapped sections during the reuniting healing process of the ramus.

2. The apparatus for providing a positive repositioning indexing reference to insure accurate repositioning of the condyle in the temporal fossa socket, said apparatus comprising,
    a template having means for adjusting the same to fit the maxillary teeth,
    anchoring means provided on the template for permitting positive anchoring of the template to the maxillary teeth,
    an indexing paddle fixed to the inner end of said template for overlying the ramus to provide a positive indexing reference to permit the upper ramus section to be accurately repositioned with its condyle received in the temporal fossa socket, and
    said template means being constructed of at least a pair of rigid sections,
    means pivotally connecting the sections together on a vertical axis to permit the angular relationship of the template sections to be adjusted to fit the teeth of different sized maxillary arches,
    said sections being of a length to overlie substantial portions of both the left and right sides of the maxillary arch and said anchoring means permitting positive anchoring to said teeth on both sides of the maxillary arch.

3. The structure set forth in claim 2 wherein said anchoring means includes at least one recess provided in said template with anchoring holes formed therein to positively connect the adhesive to the template and facilitate anchoring of the template to the maxillary teeth.

4. The structure set forth in claim 2 and a forwardly-extending gripping handle to assist in positioning and holding the template prior to its connection to the teeth of the maxillary arch.

* * * * *